US009797019B2

(12) United States Patent
Lambotte et al.

(10) Patent No.: US 9,797,019 B2
(45) Date of Patent: *Oct. 24, 2017

(54) DEVICES FOR THE DETECTION OF MULTIPLE ANALYTES IN A SAMPLE

(71) Applicant: Quidel Corporation, San Diego, CA (US)

(72) Inventors: Paul Lambotte, San Diego, CA (US); Michael Cerrito, Cardiff, CA (US); Cecille Ramirez, Murrieta, CA (US)

(73) Assignee: Quidel Corporation, San Diego, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/928,119

(22) Filed: Oct. 30, 2015

(65) Prior Publication Data

US 2016/0047005 A1 Feb. 18, 2016

Related U.S. Application Data

(60) Continuation of application No. 14/211,253, filed on Mar. 14, 2014, now Pat. No. 9,207,241, which is a continuation of application No. 12/718,739, filed on Mar. 5, 2010, now Pat. No. 8,722,426, which is a division of application No. 12/115,416, filed on May 5, 2008, now Pat. No. 7,691,644, which is a division (Continued)

(51) Int. Cl.
*G01N 33/558* (2006.01)
*C12Q 1/70* (2006.01)
*G01N 33/543* (2006.01)
*G01N 33/569* (2006.01)

(52) U.S. Cl.
CPC ....... *C12Q 1/701* (2013.01); *G01N 33/54366* (2013.01); *G01N 33/558* (2013.01); *G01N 33/56983* (2013.01); *G01N 2333/11* (2013.01); *Y10S 435/805* (2013.01); *Y10S 435/97* (2013.01); *Y10S 435/973* (2013.01); *Y10S 436/805* (2013.01); *Y10S 436/81* (2013.01)

(58) Field of Classification Search
None
See application file for complete search history.

(56) References Cited

U.S. PATENT DOCUMENTS 4,235,601 A 11/1980 Deutsch et al.
4,275,149 A 6/1981 Litman et al.
4,299,916 A 11/1981 Litman et al.
(Continued)

FOREIGN PATENT DOCUMENTS

EP 1018649 A2 7/2000
WO WO 92/21977 A1 12/1992
(Continued)

OTHER PUBLICATIONS

International Search Report from PCT/US2004/031220 mailed Feb. 4, 2005, application now published as International Publication No. WO2005/031355 on Apr. 7, 2005.

*Primary Examiner* — Chris L Chin
(74) *Attorney, Agent, or Firm* — Judy Mohr; McDermott Will & Emery LLP

(57) ABSTRACT

The present invention relates generally to an assay for detecting and differentiating multiple analytes, if present, in a single fluid sample, including devices and methods therefore.

22 Claims, 4 Drawing Sheets

Related U.S. Application Data of application No. 10/948,358, filed on Sep. 22, 2004, now Pat. No. 7,378,285.

(60) Provisional application No. 60/505,092, filed on Sep. 22, 2003.

(56) References Cited

U.S. PATENT DOCUMENTS

| | | |
|---|---|---|
| 4,366,241 A | 12/1982 | Tom et al. |
| 4,373,932 A | 2/1983 | Gribnau et al. |
| 4,486,530 A * | 12/1984 | David ................. G01N 33/542 435/7.91 |
| 4,632,901 A | 12/1986 | Valkirs et al. |
| 4,695,554 A | 9/1987 | O'Connell et al. |
| 4,703,017 A | 10/1987 | Campbell et al. |
| 4,806,311 A | 2/1989 | Greenquist |
| 4,818,677 A | 4/1989 | Hay-Kaufman et al. |
| 4,863,875 A | 9/1989 | Baily et al. |
| 4,943,522 A | 7/1990 | Eisinger et al. |
| 5,075,078 A | 12/1991 | Osikowicz et al. |
| 5,096,837 A | 3/1992 | Fan et al. |
| 5,118,428 A | 6/1992 | Sand et al. |
| 5,118,630 A | 6/1992 | Glaze |
| 5,221,616 A | 6/1993 | Kolb et al. |
| 5,223,220 A | 6/1993 | Fan et al. |
| 5,225,328 A | 7/1993 | Chang |
| 5,415,994 A | 5/1995 | Imrich et al. |
| 5,434,057 A | 7/1995 | Dorian |
| 5,521,102 A | 5/1996 | Boehringer et al. |
| RE35,306 E | 7/1996 | Chen et al. |
| 5,536,646 A | 7/1996 | Sand et al. |
| 5,541,069 A | 7/1996 | Mortensen et al. |
| 5,559,041 A | 9/1996 | Kang et al. |
| 5,602,040 A | 2/1997 | May et al. |
| 5,686,315 A | 11/1997 | Pronovost et al. |
| 5,712,172 A | 1/1998 | Huang et al. |
| 5,763,262 A | 6/1998 | Wong et al. |
| 5,766,961 A | 6/1998 | Pawlak et al. |
| 5,770,389 A * | 6/1998 | Ching ............. G01N 33/54373 250/214 A |
| 5,770,460 A | 6/1998 | Pawlak et al. |
| 5,773,234 A | 6/1998 | Pronovost et al. |
| 5,786,220 A | 7/1998 | Pronovost et al. |
| 5,804,452 A | 9/1998 | Pronovost et al. |
| 5,814,455 A | 9/1998 | Pronovost et al. |
| 5,939,331 A | 8/1999 | Burd et al. |
| 6,187,598 B1 | 2/2001 | May et al. |
| 6,210,898 B1 | 4/2001 | Bouma et al. |
| 6,306,642 B1 | 10/2001 | Nelson et al. |
| 6,352,862 B1 | 3/2002 | Davis et al. |
| 6,410,341 B1 * | 6/2002 | Freitag ............. G01N 33/54366 422/417 |
| 6,485,982 B1 | 11/2002 | Charlton |
| 6,528,325 B1 | 3/2003 | Hubscher et al. |
| 6,534,320 B2 | 3/2003 | Ching et al. |
| 6,627,459 B1 | 9/2003 | Tung et al. |
| 6,766,817 B2 | 7/2004 | Da Silva |
| 6,767,714 B2 | 7/2004 | Nazareth et al. |
| 6,790,611 B2 | 9/2004 | Lassen et al. |
| 6,855,561 B2 | 2/2005 | Jerome et al. |
| 7,378,285 B2 * | 5/2008 | Lambotte ......... G01N 33/54366 422/412 |
| 7,691,644 B2 * | 4/2010 | Lambotte ......... G01N 33/54366 422/412 |
| 8,722,426 B2 * | 5/2014 | Lambotte ......... G01N 33/54366 422/420 |
| 9,207,241 B2 * | 12/2015 | Lambotte ......... G01N 33/54366 |
| 2002/0004246 A1 * | 1/2002 | Daniels ................ G01N 33/558 436/514 |
| 2002/0115062 A1 | 8/2002 | Fletcher et al. |
| 2003/0049167 A1 * | 3/2003 | Jerome .............. G01N 21/8483 422/420 |
| 2003/0129767 A1 | 7/2003 | Bautista et al. |
| 2003/0157699 A1 | 8/2003 | Jerome et al. |
| 2003/0161762 A1 | 8/2003 | Caron et al. |
| 2004/0219690 A1 | 11/2004 | Choi et al. |
| 2005/0130120 A1 | 6/2005 | Lambotte et al. |
| 2009/0029453 A1 | 1/2009 | Lambotte et al. |
| 2010/0159444 A1 | 6/2010 | Lambotte et al. |
| 2014/0199685 A1 | 7/2014 | Lambotte et al. |

FOREIGN PATENT DOCUMENTS

| | | |
|---|---|---|
| WO | WO 94/01775 A1 | 1/1994 |
| WO | WO 99/36777 A1 | 7/1999 |
| WO | WO 00/63697 A1 | 10/2000 |
| WO | WO 01/57522 A2 | 8/2001 |
| WO | WO 2005/031355 A1 | 4/2005 |

\* cited by examiner

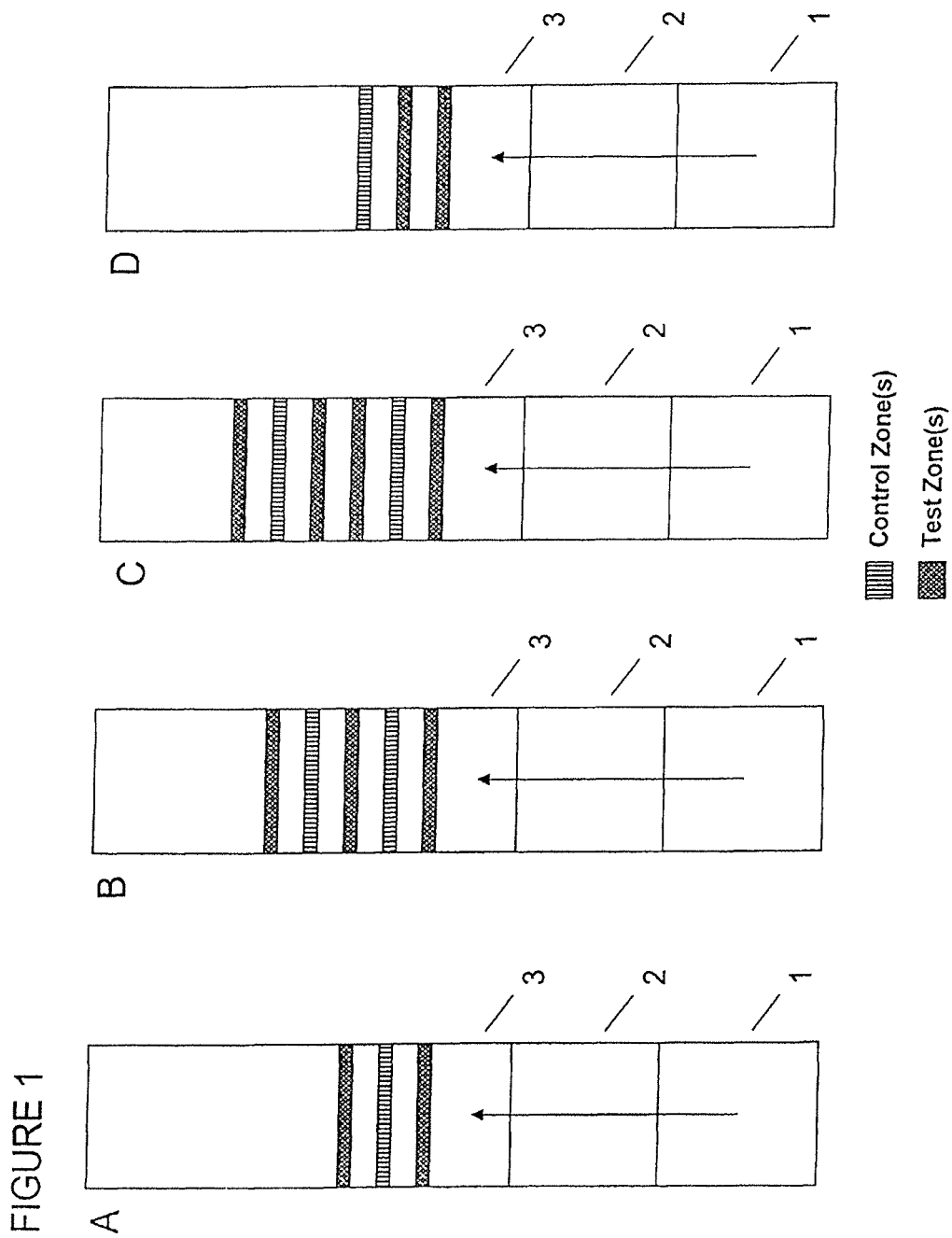

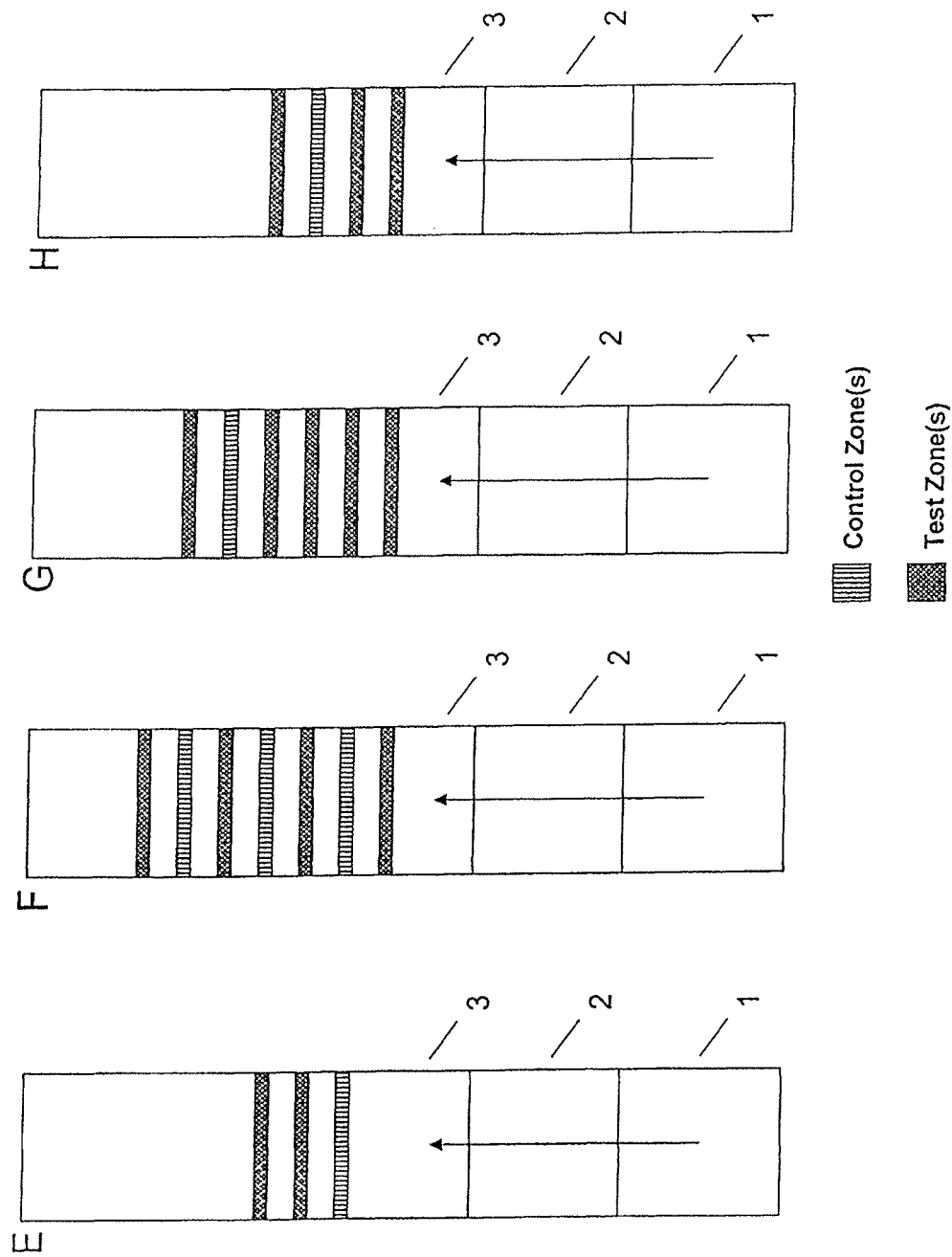

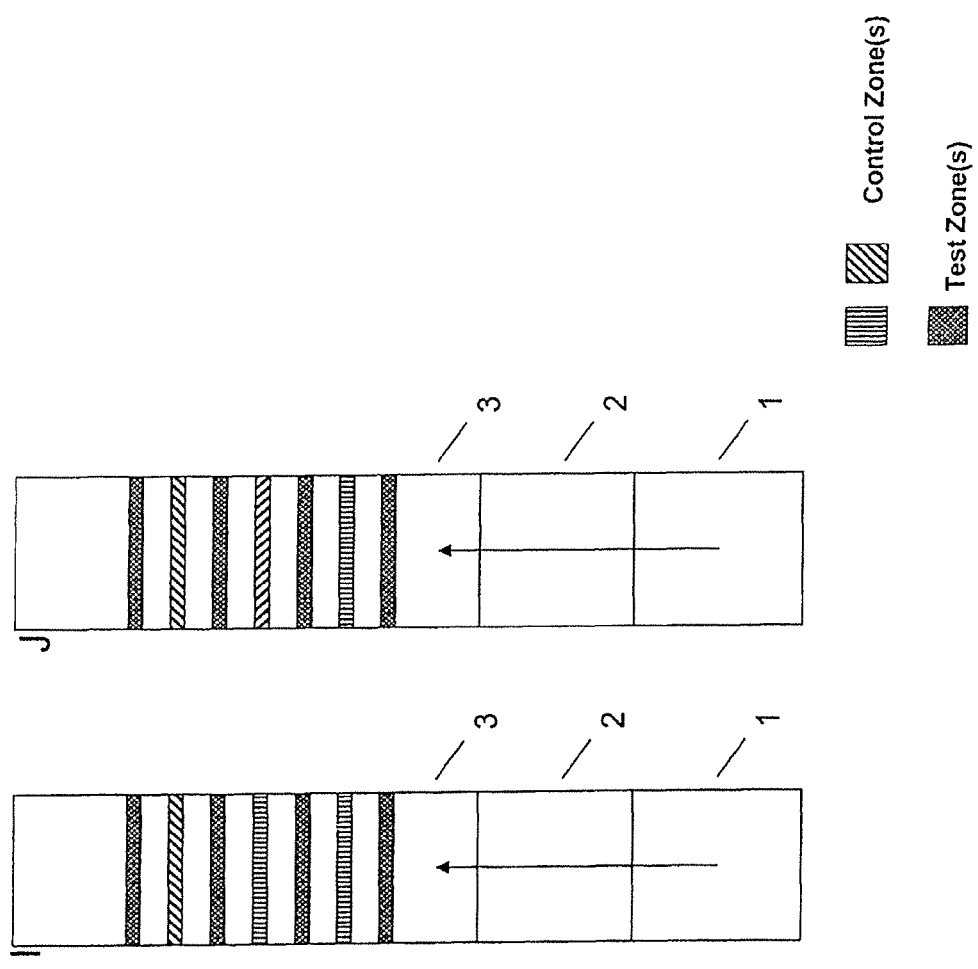

DEVICES FOR THE DETECTION OF MULTIPLE ANALYTES IN A SAMPLE

CROSS-REFERENCE TO RELATED APPLICATIONS

This application is a continuation application of U.S. application Ser. No. 14/211,253 filed Mar. 14, 2014, now U.S. Pat. No. 9,207,241, issued on Dec. 8, 2015, which is continuation application of U.S. application Ser. No. 12/718,739, filed Mar. 5, 2010, now U.S. Pat. No. 8,722,426, issued on May 13, 2014, which is a divisional of U.S. application Ser. No. 12/115,416, filed May 5, 2008, now U.S. Pat. No. 7,691,644, issued on Apr. 6, 2010, which is a divisional of U.S. application Ser. No. 10/948,358, filed Sep. 22, 2004, now U.S. Pat. No. 7,378,285, issued on May 27, 2008, which claims priority benefit of U.S. Provisional Application No. 60/505,092, filed Sep. 22, 2003. The contents of these applications are incorporated by reference in their entirety.

TECHNICAL FIELD

The present invention relates generally to an assay for detecting and differentiating multiple analytes, if present, in a single fluid sample, including devices and methods therefor.

BACKGROUND OF THE INVENTION

The field of rapid diagnostic testing has evolved for many years to permit the detection of analytes in a variety of sample types. The use of polyclonal antibodies was followed by the use of monoclonal antibodies to generate assays with high specificity for a number of analytes, including hormones, blood cells, drugs and their metabolites, as well as the antigens of infectious agents including Strep A, Strep B, *Chlamydia*, HIV, RSV, influenza A and influenza B and many others. The visible signal generated by enzyme-catalyzed reactions or by the accumulation of a visible signal at the level of a test line has also resulted in rapid development of highly sensitive results. Many of the rapid immunoassay-based tests include a solid housing encasing a test strip. However, recently, immunochromatographic assays have been manufactured which do not have solid housings. Such tests, referred to as dipsticks, can be dipped directly into a tube containing a pre-determined amount of the liquid sample of interest. The extremity of the dipstick containing a sample-receiving pad is generally brought in contact with a liquid sample, and the liquid migrates up the flow path. Advantages of the dipstick format include ease of use and minimum handling, which reduces the opportunities for contamination and procedural errors, and lowers manufacturing costs.

One disadvantage of current immunochromatographic dipsticks is that they can only detect the presence of a single analyte. Often these devices are limited because there is no provision to mark the location of possible multiple test lines along the flow path. In the field of chemical urinalysis, dipsticks carrying multiple pads, each specific for a urine analyte to be detected and measured, the dipstick is dipped into the urine sample, then removed from the container, blotted to eliminate excess urine, and applied against a template in order to read the results. These devices are capable of evaluating multiple analytes, but are problematic. For example, such devices increase the chances of contamination by carry-over of material from one device to another, with the consequence of potentially inaccurate results. Moreover, this format exposes the user to potential contamination via removing the strip from the urine sample, blotting it on an absorbent paper, which becomes contaminated, applying it against the template, which often is the exterior wall of the product container, thereby contaminating the product package itself. Further, as indicated, an external template is required to read results.

It is recognized in a variety of fields that the use of single analyte rapid tests is often limiting, for example, because only one analyte at a time can be evaluated. The advantage of rapidity is therefore challenged by the limitation of current assays as adjuncts to the diagnosis of a disease state. For instance, the pediatric units have to make differential diagnostics of Flu A, Flu B, RSV and other upper respiratory viruses, on infants that are in need of urgent care. The availability of rapid test panels would greatly facilitate the doctors' efforts to diagnose the condition, and therefore to take the appropriate course of action faster, more easily, and at lower cost. To date, no such assay has been developed that allows the differential diagnostic of two or more analytes on a single test strip, in a minimally involving procedure.

In summary, chemical urinalysis dipstick assays have been used for many years to determine the presence (or amount) of multiple analytes in a urine sample; however, the technology used to perform such assays not only has undesirable use characteristics but is not readily transferable to immunologic based assays (dipstick or lateral flow) which require flow of sample through the assay device rather than immersion of the device (in particular immersion of the test portion of the device) into a sample. For example, with respect to the use of chemical urinalysis dipsticks, the fact that they must be submerged into the urine sample, removed and blotted of excess urine then placed in physical contact (or very close proximity) with an external, typically reusable (and hence contaminable), test results panel (i.e., template) is not just undesirable but unsafe, particularly if the sample contains contagious agents such as virus or bacteria. Further, because immunologic based assays typically employ at least two, generally sequential reactions (for example a labeling followed by a capture (test) reaction), they are not amenable to submersion into a sample in the same manner as the chemical urinalysis dipsticks. Thus, there is a need in the art for devices and methods that addresses these problems in the art. The present invention addresses these and other related needs in the art.

SUMMARY OF INVENTION

The present invention provides analytical devices, particularly immunoassay devices, capable of determining the presence and/or amount of multiple analytes in a fluid sample, permitting more complete diagnosis or analysis of said sample. Advantageously, the present devices may be formatted as dipsticks or lateral flow devices, in either case not requiring an external test results panel for determination of test results. By positioning the multiple test and/or control zones in predetermined patterns on the test devices in accordance with the present invention, the need for an external test results panel, or even markings on a test device housing, is eliminated. By way of example, in a preferred embodiment, a single control zone is positioned between two test zones, each test zone testing for the presence or amount of a different analyte. It has heretofore been assumed that a control zone must be located downstream of a test zone in order function as control zone. However, the present inventors have discovered that such is not necessary and, rather, that one or more control zones may be employed in immunoassay devices not only to provide an indication of assay completion and/or operability but also of the relative location of one or more test lines, thereby permitting rapid differentiation of analytes within a fluid sample in a single immunoassay test device.

In an embodiment of the present disclosure, a device is provided for the detection of multiple analytes in a fluid sample, which device comprises: a matrix defining an axial flow path, the matrix comprising: i) a sample receiving zone at an upstream end of the flow path that receives the fluid sample, ii) a label zone positioned within the flow path and downstream from the sample receiving zone, said label zone comprising one or more labeled reagents which are capable of binding one or more analytes to form labeled analytes and are mobilizable in the presence of fluid sample, iii) one or more test zones positioned within the flow path and downstream from the label zone, wherein each of the one or more test zones contain means which permit the restraint of a different labeled analyte in each test zone or a combination of different labeled analyte in a single test zone, and wherein restrained labeled analyte is detectable within each test zone, and iv) one or more control zones positioned within the flow path and downstream from the label zone, wherein the one or more control zones incorporate means which permit the indication of the completion of an assay. In the most frequent embodiments, the device incorporates means to restrain and thereby detect two or more different labeled analytes in a sample. Also, in frequent embodiments, the device comprises a dipstick assay device. In occasional embodiments, the device comprises two or three or more test zones and two or more control zones.

The present device permits the detection of multiple analytes in a sample without reference to an external template. Moreover, frequently the device comprises a dipstick assay that lacks an external housing. In general, the analytes comprise analytes of interest and further comprise those provided herein, among others. Frequently, the present devices are useful for assaying a particular panel of analytes. Also frequently, the present devices are useful to simultaneously detect two or more different analytes in a sample. On occasion the present device and methods are useful to detect a panel of analytes of interest selected from an influenza panel (comprising test zones containing reagents capable of restraining a selection of influenza A, influenza B, respiratory syncytial virus (RSV), adenovirus, rhinovirus and/or parainfluenza virus), a panel comprising one or more of *streptococcus pneumoniae, mycoplasma pneumoniae* and/or *Chlamydia*, an HIV panel, a Lupus panel, an *H. Pylori* panel, a *toxoplasma* panel, a herpes panel, a *Borrelia* panel, a rubella panel, a cytomegalovirus panels, a rheumatoid arthritis panel, or an Epstein-Barr panel, among others.

In one preferred aspect. each of the one or more test zones lie in fluid communication with one another. Moreover, in another aspect, the one or more test zones lie in fluid communication with one or more control zones. In a further aspect, the presently contemplated devices do not utilize one or a plurality of wells, rather a matrix defining an axial flow path is utilized. In a frequent embodiment, a device in accordance with the present disclosure contains a single sample receiving zone that lies in fluid communication with the one or more test zones.

In frequent embodiments, the control zone is positioned between the one or more test zones. In occasional embodiments, the positioning of the control zone between the one or more test zones comprises positioning one control zone between two test zones. Also in occasional embodiments, the positioning of the control zone between the one or more test zones comprises multiple test zones and multiple control zones, wherein each control zone is positioned between two test zones, in an alternating arrangement. Frequently, the control zone is positioned upstream of a test zone. Also frequently, the control zone is positioned downstream of a test zone. In occasional embodiments, the control zone is positioned downstream of each or all of the one or more test zones. In another embodiment, the test and control zones are positioned in an alternating format within the flow path beginning with a test zone positioned upstream of any control zone.

In one embodiment, each of the one or more test zones contain means comprising an immobilized reagent capable of specifically binding a unique analyte. Thus, in this embodiment, each of the one or more test zones contain an immobilized reagent capable of specifically binding a particular analyte, wherein each of the immobilized reagents is capable of binding a different analyte than any other immobilized reagent within another test zone in the device. These means can comprise any of a variety of specific binding pair members as described elsewhere herein. On occasion, the means which permit the restraint of a different labeled analyte in each test zone comprise an immobilized capture reagent.

In one aspect, the test zones can be provided in any of a variety shapes and configurations with the limitation that each particular test zone is detectably distinguishable from other test zones, if present, and the control zone(s) in the presence of labeled analyte, if present, restrained in that test zone. In a related aspect, the control zones can be provided in any of a variety shapes and configurations with the limitation that each particular control zone is detectably distinguishable from other control zones, if present, and the test zones upon completion of an assay.

In another embodiment, the label zone comprises multiple labeled reagents, wherein each of the multiple labeled reagents is capable of specifically binding a unique analyte. In occasional embodiments, the labeled reagent is a reagent capable of binding any or all of the multiple analytes, if present, in the sample. Frequently, each of the labeled reagents is detectably distinguishable from one another. Also frequently, the label component of the labeled reagent is selected from the group consisting of a chemiluminescent agent, a particulate label, a colloid label, a colorimetric agent, an energy transfer agent, an enzyme, a fluorescent agent and a radioisotope. In occasional embodiments, the labeled reagents comprise different colored labeled reagents. For example, the labeled reagent can comprise 2, 3, 4, 5, or 6 or more different colored particulate reagents. Particulate label colors comprising red, blue, black, purple, and other high-contrast colors are frequently utilized in the present embodiments. In frequent embodiments, the colored particulate label comprises a colored latex particulate label. In another frequent embodiment, the colored label comprises a Carbon, Gold or Selenium colored colloid label. On occasion, the use of different colored particulate labeled reagents allows for the detection of multiple analytes via the observation of different detectable signals (e.g., different colors) in any one or more of the one or more test zones as a result of the restraint of different labeled analyte in each test zone. In a less occasional embodiment, the labeled reagent can comprise a mixture of any of a variety of detectable labeling schemes in one device such that each analyte can become labeled by a different labeled reagent to provide a different detectable signal.

In occasional embodiments, a test zone may contain one or more immobilized reagents capable of specifically binding a unique analyte, such that multiple labeled analytes may become restrained and detectible in the test zone. In this embodiment there may be multiple analytes of interest for the device, however, frequently only one of these analytes is present, if at all, at one time in the fluid sample. Thus, multiple labeled reagents are useful in this embodiment which are both analyte specific and detectably distinguishable (i.e., different colors). For example, a device of the present embodiment is capable of detecting Influenza A or influenza B antigen, if present, in a single sample. In the case of influenza A, a red-colored labeled reagent that is capable of specifically binding influenza A may be used, which would result in the development of a red-colored test zone after completion of the assay of a fluid sample containing influenza A analyte. In the case of Influenza B, a blue-colored labeled reagent that is capable of specifically binding influenza B may be used, which would result in the development of a blue-colored test zone after completion of the assay of a fluid sample containing influenza B analyte. One of skill in the art would recognize that the colors may be alternated and/or other detectibly distinguishable labeling means contemplated herein may be utilized. Frequently, such test zones can be deposited as single zones containing a mixture of capture reagent, or as adjacent zones of single capture reagents. On occasion, in the present embodiment, multiple analytes of interest are present together in the fluid sample, which then become labeled subsequent to contact with the device and restrained in the test zone. Thus, multiple labeled analytes may be restrained in a single test zone.

In another embodiment, the sample receiving zone and the label zone comprise separate components in fluid-flow contact. In a frequent embodiment, the one or more test zones and the control zone are positioned within a test region. Moreover, frequently, the sample receiving zone, label zone and the test region comprise separate components in fluid-flow contact. Also frequently, the test region comprises nitrocellulose or other material suitable for immobilization of test and control reagents, and/or is laminated on a plastic backing material. On occasion, the matrix is positioned within a housing comprising a support and optionally a cover, wherein the housing contains a sample-receiving aperture and one or more observation ports. In occasional embodiments, the control zone comprises a mark that is detectable within the test region when the test region is in a moist state. In this embodiment the test region comprises a material that is opaque in a dry state and transparent in a moist state such that the mark become visible as the liquid sample moistens the test region.

In a further embodiment, the device is capable of detecting influenza A and/or influenza B, if present, in a single sample. In occasional embodiments, each of the multiple analytes are selected from the group consisting of a toxin, an organic compound, a protein, a peptide, a microorganism, a bacteria, a virus, an amino acid, a nucleic acid, a carbohydrate, a hormone, a steroid, a vitamin, a drug, an antibody, and a hapten.

In another further embodiment, the number of control zones is represented by the variable "n" and the number of test zones is represented by the variable "n+1," and wherein the test zones and control zones are positioned in a series comprising an alternating format, wherein the zone arranged at the most downstream position in the series comprises a test zone. The variable "n" often refers to 2 test zones. However, on occasion, the variable "n" refers to between 2 to about 5 test zones. Thus, on occasion, 2, 3, 4, 5 or more test zones are positioned on the device. Frequently, each of the test zones permit the restraint of a different analyte. On occasion, a device is provided that is capable of detecting a number of different analytes represented by the variable "n," wherein the number of control zones and the number of different analytes capable of being detected by the device are equal. Also on occasion, a device is provided that is capable of detecting a number of different analytes represented by the variable "n+1," wherein the number of test zones and the number of different analytes capable of being detected by the device are equal.

In frequent embodiments a device for the detection of multiple analytes in a fluid sample is provided, wherein the device comprises: a matrix defining an axial flow path, the matrix comprising: i) a sample receiving zone at an upstream end of the flow path that receives the fluid sample; ii) a label zone, within the flow path and downstream from the sample receiving zone, comprising a first and second labeled reagent, each of which specifically bind an analyte to form a labeled analyte and are mobilizable in the presence of fluid sample; and iii) a test region comprising a first test zone, a second test zone and a control zone, wherein the control zone is positioned between the first and second test zones within the flow path, wherein each of the first and second test zones contain means which permit the detection of a different analyte in each test zone, and wherein the control zone incorporates means which allow for the indication of the completion of an assay. In occasional embodiments, the first zone is positioned upstream from the control zone within the flow path and the second zone is positioned downstream from the control zone within the flow path.

In another embodiment, methods are provided for the detection of one or more analytes in a fluid sample. For example, a method is provided for the detection of multiple analytes in a fluid sample, comprising: i) contacting a device of the type described above with a fluid sample suspected of containing one or more analytes, and wherein each of the one or more test zones in the device contains means which permit the restraint of a different labeled analyte or combination of labeled analytes in each test zone; and ii) detecting one or more labeled analytes restrained in the one or more test zones. Frequently the device comprises a dipstick-type device. In general, the analytes of interest comprise those provided herein, among others. Frequently, the present methods are useful for assaying a particular panel of analytes. Also frequently, the present methods are useful to simultaneously detect two or more different analytes in a sample. Commonly the present devices and methods are utilized to diagnose a medical condition. Also commonly, the present devices and methods aid in guiding therapeutic decisions. On occasion, the present method steps may be practiced at different locations, and by different entities.

These and other features and advantages of the present invention will be apparent from the following detailed description, examples and claims.

BRIEF DESCRIPTION OF THE DRAWINGS

FIG. 1(A-J) depicts various example configurations of the test and control zones within the presently contemplated devices. The arrow in each Figure indicates the general direction of fluid sample flow after initial contact with the device. The boxes containing vertical lines and/or the diagonal lines depict control zones, and the boxes containing crosshatched lines depict test zones. FIG. 1(A-J) further depicts the sample receiving zone [1], the label zone [2] and the test region[3]. The present devices are not intended to be limited to the aspects indicated in the depicted embodiments, other configurations are contemplated. Moreover, the depicted aspects are not necessarily presented to scale.

DETAILED DESCRIPTION OF THE INVENTION

Figure 2:
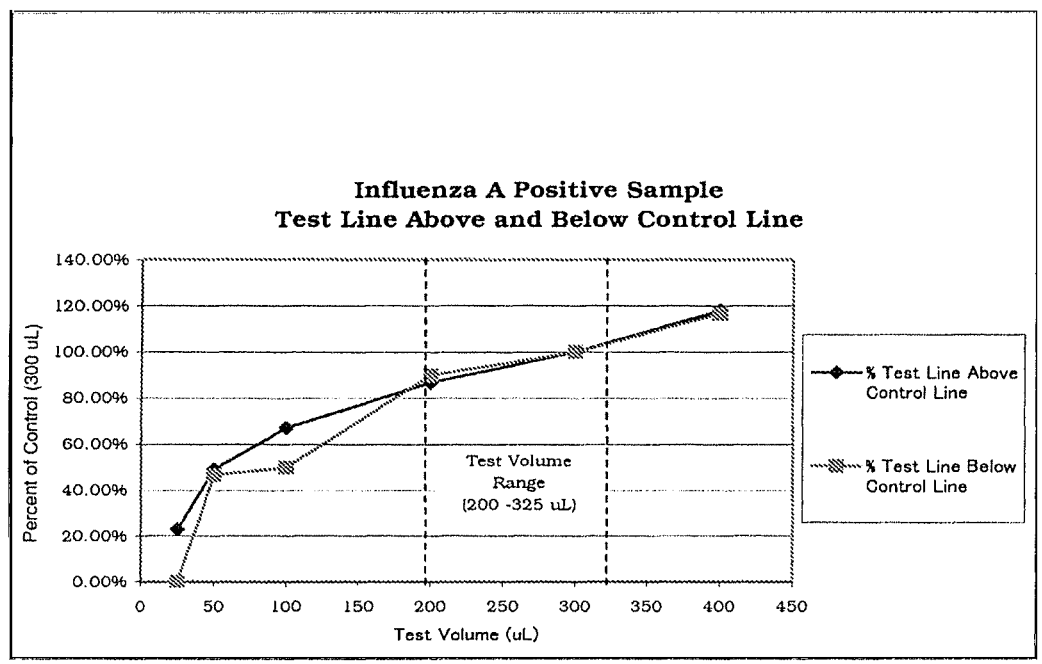
FIG. 2 is a graph depicting the ratio of test zone and control zone signals for different volumes of sample in exemplary devices.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more." The use of the phrase "one or more" herein does not alter this intended meaning for the terms "a" or "an."

As used herein, "disease or disorder" refers to a pathological condition in an organism resulting from, e.g., infection or genetic defect, and characterized by identifiable symptoms.

As used herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

"Fluid sample" refers to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay. Typically, the sample is an aqueous solution or biological fluid as described in more detail below.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte. The selection and pretreatment of biological, industrial, and environmental samples prior to testing is well known in the art and need not be described further.

As used herein, the term "specifically binds" refers to the binding specificity of a specific binding pair. "Specific pair binding member" refers to a member of a specific binding pair, i.e., two different molecules wherein one of the molecules specifically binds with the second molecule through chemical or physical means. The two molecules are related in the sense that their binding with each other is such that they are capable of distinguishing their binding partner from other assay constituents having similar characteristics. The members of the specific binding pair are referred to as ligand and receptor (antiligand), sbp member and sbp partner, and the like. A molecule may also be a sbp member for an aggregation of molecules; for example an antibody raised against an immune complex of a second antibody and its corresponding antigen may be considered to be an sbp member for the immune complex.

In addition to antigen and antibody specific binding pair members, other specific binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), metals and their chelators, and the like. Furthermore, specific binding pairs can include members that are analogs of the original specific binding member, for example an analyte-analog or a specific binding member made by recombinant techniques or molecular engineering.

An sbp member is analogous to another sbp member if they are both capable of binding to another identical complementary sbp member. Such an sbp member may, for example, be either a ligand or a receptor that has been modified by the replacement of at least one hydrogen atom by a group to provide, for example, a labeled ligand or labeled receptor. The sbp members can be analogous to or complementary to the analyte or to an sbp member that is complementary to the analyte.

If the specific binding member is an immunoreactant it can be, for example, an antibody, antigen, hapten, or complex thereof. If an antibody is used, it can be a monoclonal or polyclonal antibody, a recombinant protein or antibody, a chimeric antibody, a mixture(s) or fragment(s) thereof, as well as a mixture of an antibody and other specific binding members. The details of the preparation of such antibodies and their suitability for use as specific binding members are known to those skilled in the art.

"Antigen" shall mean any compound capable of binding to an antibody, or against which antibodies can be raised.

"Antibody" refers to a polypeptide substantially encoded by an immunoglobulin gene or immunoglobulin genes, or fragments thereof. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies or fragment thereof made by recombinant methods.

"Analyte" refers to the compound or composition to be detected or measured and which has at least one epitope or binding site. The analyte can be any substance for which there exists a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunologically detected. That is, the analyte, or portion thereof, will be antigenic or haptenic having at least one determinant site, or will be a member of a naturally occurring binding pair.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof. A non-exhaustive list of exemplary analytes is set forth in U.S. Pat. No. 4,366,241, at column 19, line 7 through column 26, line 42, the disclosure of which is incorporated herein by reference. Further descriptions and listings of representative analytes are found in U.S. Pat. Nos. 4,299,916; 4,275,149; and 4,806,311, all incorporated herein by reference.

"Labeled reagent" refers to a substance comprising a detectable label attached with a specific binding member. The attachment may be covalent or non-covalent binding, but the method of attachment is not critical to the present invention. The label allows the label reagent to produce a detectable signal that is related to the presence of analyte in the fluid sample. The specific binding member component of the label reagent is selected to directly bind to the analyte or to indirectly bind the analyte by means of an ancillary specific binding member, which is described in greater detail hereinafter. The label reagent can be incorporated into the test device at a site upstream from the capture zone, it can be combined with the fluid sample to form a fluid solution, it can be added to the test device separately from the test sample, or it can be predeposited or reversibly immobilized at the capture zone. In addition, the specific binding member may be labeled before or during the performance of the assay by means of a suitable attachment method.

"Label" refers to any substance which is capable of producing a signal that is detectable by visual or instrumental means. Various labels suitable for use in the present invention include labels which produce signals through either chemical or physical means. Such labels can include enzymes and substrates, chromogens, catalysts, fluorescent compounds, chemiluminescent compounds, and radioactive labels. Other suitable labels include particulate labels such as colloidal metallic particles such as gold, colloidal non-metallic particles such as selenium or tellurium, dyed or colored particles such as a dyed plastic or a stained microorganism, organic polymer latex particles and liposomes, colored beads, polymer microcapsules, sacs, erythrocytes, erythrocyte ghosts, or other vesicles containing directly visible substances, and the like. Typically, a visually detectable label is used as the label component of the label reagent, thereby providing for the direct visual or instrumental readout of the presence or amount of the analyte in the test sample without the need for additional signal producing components at the detection sites.

The selection of a particular label is not critical to the present invention, but the label will be capable of generating a detectable signal either by itself, or be instrumentally detectable, or be detectable in conjunction with one or more additional signal producing components, such as an enzyme/substrate signal producing system. A variety of different label reagents can be formed by varying either the label or the specific binding member component of the label reagent; it will be appreciated by one skilled in the art that the choice involves consideration of the analyte to be detected and the desired means of detection. As discussed below, a label may also be incorporated used in a control system for the assay.

For example, one or more signal producing components can be reacted with the label to generate a detectable signal. If the label is an enzyme, then amplification of the detectable signal is obtained by reacting the enzyme with one or more substrates or additional enzymes and substrates to produce a detectable reaction product.

In an alternative signal producing system, the label can be a fluorescent compound where no enzymatic manipulation of the label is required to produce the detectable signal. Fluorescent molecules include, for example, fluorescein, phycobiliprotein, rhodamine and their derivatives and analogs are suitable for use as labels in such a system.

The use of dyes for staining biological materials, such as proteins, carbohydrates, nucleic acids, and whole organisms is documented in the literature. It is known that certain dyes stain particular materials preferentially based on compatible chemistries of dye and ligand. For example, Coomassie Blue and Methylene Blue for proteins, periodic acid-Schiff s reagent for carbohydrates, Crystal Violet, Safranin O, and Trypan Blue for whole cell stains, ethidium bromide and Acridine Orange for nucleic acid staining, and fluorescent stains such as rhodamine and Calcofluor White for detection by fluorescent microscopy. Further examples of labels can be found in, at least, U.S. Pat. Nos. 4,695,554; 4,863,875; 4,373,932; and 4,366,241, all incorporated herein by reference.

"Signal producing component" refers to any substance capable of reacting with another assay reagent or with the analyte to produce a reaction product or signal that indicates the presence of the analyte and that is detectable by visual or instrumental means. "Signal production system", as used herein, refers to the group of assay reagents that are needed to produce the desired reaction product or signal.

"Observable signal" as used herein refers to a signal produced in the claimed devices and methods that is detectable by visual inspection. Without limitation, the type of signal produced depends on the label reagents and marks used (described herein). Generally, observable signals indicating the presence or absence of an analyte in a sample may be evident of their own accord, e.g., plus or minus signs or particularly shaped symbols, or may be evident through the comparison with a panel such as a color indicator panel.

"Axial flow" as used herein refers to lateral, vertical or transverse flow through a particular matrix or material comprising one or more test and/or control zones. The type of flow contemplated in a particular device, assay or method varies according to the structure of the device. Without being bound by theory, lateral, vertical or transverse flow may refer to flow of a fluid sample from the point of fluid contact on one end or side of a particular matrix (the upstream or proximal end) to an area downstream (or distal) of this contact. The downstream area may be on the same side or on the opposite side of the matrix from the point of fluid contact. For example, in vertical flow devices of the present invention, axial flow may progress vertically from and through a first member (top to bottom) to a second member and from there on to an absorbent medium. By way of further example, and as will be appreciated by those of skill in the art, in a vertical flow device configured, for example, as a dipstick, a fluid sample may flow literally up the device, in which case however, the point of first contact of the fluid sample to the device is nonetheless considered the upstream (i.e., proximal) end and the point of termination of flow the downstream (i.e., distal) end.

"Absorbent material" as used herein refers to material used in vertical flow devices and assays that allows and promotes sample flow through the first and second members. Such materials may be as described in, e.g., U.S. Pat. No. 4,632,901, such as, for example, fibrous materials such as cellulose acetate fibers, cellulose or cellulose derivatives, polyester, or polyolefin. Generally, the absorbent material, as used herein, should maintain direct or intimate contact with the second member in order to promote fluid flow therethrough. Contemplated absorbent materials having fluid absorptive qualities are generally compressible and may be compressed in devices of the present invention to ensure contact with the second member or positive control element.

As used herein the phrase "mark that is detectable within the test region when the test region is in a moist state" refers to the type of mark described, for example in U.S. patent application Ser. No. 09/950,366, filed, Sep. 10, 2001, currently pending and published as U.S. Patent Application Publication No. 20030049167, and Ser. No. 10/241,822, filed Sep. 10, 2002, currently pending and published as U.S. Patent Application Publication No. 20030157699.

As used herein the terms "upstream" and "downstream" refer to the direction of fluid sample flow subsequent to contact of the fluid sample with a representative device of the present disclosure, wherein, under normal operating conditions, the fluid sample flow direction runs from an upstream position to a downstream position. For example, when fluid sample is initially contacted with the sample receiving zone, the fluid sample then flows downstream through the label zone and so forth.

As used herein the phrase "completion of an assay" refers to axial flow of applied liquid sample suspected of containing one or more analytes through a representative device, downstream of at least one test zone and at least one control zone. Thus, as used herein multiple assays could be completed in a single device which comprises multiple pairs of alternating test and control zones. More commonly, the phrase completion of assay refers to axial flow of applied liquid sample suspected of containing one or more analytes through a representative device, downstream of all test and control zones on or in the device.

B. Test Devices

The present description provides for the development and use of single or multiple control zones in a single immunoassay device that are positioned in a predetermined manner relative to individual test zones thereby allowing easy identification of each of the one or more analytes of interest tested for in the device. The present description further provides for the making of control zones of various shapes, physical or chemical identities, and colors. In part, the use of such control zones allows for immunoassay devices, particularly including dipsticks, that are easy to use, and allow for the identification of multiple analytes during a single assay procedure.

The present description further provides means to build a rapid, multi-analyte assay, which is needed in many fields of environmental monitoring, medicine, particularly in the field of infectious disease. For example, contemplated devices include those useful for the differential diagnosis of Flu A or Flu B, which may result in different treatments, or the differential diagnosis of Flu A, Flu B, and/or RSV in one step. Such devices permit the use of a single sample for assaying multiple analytes at once, and beneficially allows for a considerable reduction of the hands-on time and duration of the diagnostic process for the benefit of the doctor, or user in general.

A variety of analytes may be assayed utilizing devices and methods of the present disclosure. In a particular device useful for assaying for one or more analytes of interest in a sample, the collection of analytes of interest may be referred to as a panel. For example, a panel may comprise any combination (or all of) of influenza A, influenza B, respiratory syncytial virus (RSV), adenovirus, and parainfluenza virus. Another panel may comprise testing for a selection of one or more of upper respiratory infection including, for example, *streptococcus pneumoniae, mycoplasma* and/or *pneumoniae*. Yet another panel can be devised for the diagnosis of sexually transmitted disease including, for example, *Chlamydia, Trichomonas* and/or Gonorrhea.

On occasion a panel may optionally include a variety of other analytes of interest, including SARS-associated coronavirus, influenza C; a hepatitis panel comprising a selection of hepatitis B surface Ag or Ab, hepatitis B core Ab, hepatitis A virus Ab, and hepatitis C virus; a phospholipids panel comprising a selection of Anticardiolipin Abs (IgG, IgA, and IgM Isotypes); an arthritis panel comprising a selection of rheumatoid factor, antinuclear antibodies, and Uric Acid; an Epstein Barr panel comprising a selection of Epstein Barr Nuclear Ag, Epstein Barr Viral Capsid Ag, and Epstein Barr Virus, Early Antigen; other panels include HIV panels, Lupus panels, *H. Pylori* panels, *toxoplasma* panels, herpes panels, *Borrelia* panels, rubella panels, cytomegalovirus panels, and many others. One of skill in art would understand that a variety of panels may be assayed via the immunoassays described herein. See, e.g., CURRENT PROTOCOLS IN IMMUNOLOGY (Coligan, John E. et. al., eds. 1999).

Other fields of interest include the diagnosis of veterinary diseases, analysis of meat, poultry, fish for bacterial contamination, inspection of food plants, restaurants, hospitals and other public facilities, analysis of environmental samples including water for beach, lakes or swimming pool contamination. Analytes detected by these tests include viral and bacterial antigens as well as chemicals including, for example, lead, pesticides, hormones, drugs and their metabolites, hydrocarbons and all kinds of organic or inorganic compounds.

The present disclosure provides a test device, particularly immunoassay devices, for determining the presence or absence of multiple analytes in a fluid sample. In general, a test device of the present disclosure includes a matrix defining an axial flow path. Typically, the matrix further includes a sample receiving zone, a label zone, a test zone and a control zone. In frequent embodiments, a test region comprises the test and control zones. In a related embodiment, the matrix further includes an absorbent zone disposed downstream of the test region. Moreover, in preferred embodiments, the test region, which comprises the test and control zones, is observable.

Numerous analytical devices known to those of skill in the art may be adapted in accordance with the present invention, to detect multiple analytes. By way of example, dipstick, lateral flow and flow-through devices, particularly those that are immunoassays, may be modified in accordance herewith in order to detect and distinguish multiple analytes. Exemplary lateral flow devices include those described in U.S. Pat. Nos. 4,818,677, 4,943,522, 5,096,837 (RE 35,306), 5,096,837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5,939,331, 6,306,642. Other lateral flow devices that may be modified for use in distinguishable detection of multiple analytes in a fluid sample include U.S. Pat. Nos. 4,703,017, 6,187,598, 6,352,862, 6,485,982, 6,534,320 and 6,767,714. Exemplary dipstick devices include those described in U.S. Pat. Nos. 4,235,601, 5,559,041, 5,712,172 and 6,790,611. It will be appreciated by those of skill in the art that the aforementioned patents may and frequently do disclose more than one assay configuration and are likewise referred to herein for such additional disclosures. Advantageously, the improvements described are applicable to various assay, especially immunoassay, configurations.

In a frequent embodiment, the sample receiving zone accepts a fluid sample that may contain analytes of interest. In another embodiment, the sample receiving zone is dipped into a fluid sample. A label zone is located downstream of the sample receiving zone, and contains one or more mobile label reagents that recognize, or are capable of binding the analytes of interest. Further, a test region is disposed downstream from the label zone, and contains test and control zones. The test zone(s) generally contain means which permit the restraint of a particular analyte of interest in each test zone. Frequently, the means included in the test zone(s) comprise an immobilized capture reagent that binds to the analyte of interest. Generally the immobilized capture reagent specifically binds to the analyte of interest. Although, on occasion, the means which permit the restraint of a particular analyte of interest in each test zone comprise another physical, chemical or immunological means for specifically restraining an analyte of interest. Thus, as the fluid sample flows along the matrix, the analyte of interest will first bind with a mobilizable label reagent in the label zone, and then become restrained in the test zone. In occasional embodiments, the test region is comprised of a material that is opaque in a dry state and transparent in a moist state. Thus, when a control zone comprising a mark on the device is utilized, this mark is positioned about the test region such that it becomes visible within the test region when the test region is in a moist state.

In another preferred embodiment, the fluid sample flows along a flow path running from the sample receiving zone (upstream), through the label zone, and then to the test and control zones (together comprised in a test region) (downstream). Optionally, the fluid sample may thereafter continue to the absorbent zone.

In one embodiment, the sample receiving zone is comprised of an absorbent application pad. Suitable materials for manufacturing absorbent application pads include, but are not limited to, hydrophilic polyethylene materials or pads, acrylic fiber, glass fiber, filter paper or pads, desiccated paper, paper pulp, fabric, and the like. For example, the sample receiving zone may be comprised of a material such as a nonwoven spunlaced acrylic fiber, i.e., New Merge (available from DuPont) or HDK material (available from HDK Industries, Inc.). In a related embodiment, the sample receiving zone is constructed from any material that is capable of absorbing water.

In another embodiment, the sample receiving zone is comprised of any material from which the fluid sample can pass to the label zone. Further, the absorbent application pad can be constructed to act as a filter for cellular components, hormones, particulate, and other certain substances that may occur in the fluid sample. Application pad materials suitable for use by the present invention also include those application pad materials disclosed in U.S. Pat. No. 5,075,078, incorporated herein by reference.

The functions of the sample receiving zone may include, for example: pH control/modification and/or specific gravity control/modification of the sample applied, removal or alteration of components of the sample which may interfere or cause non-specific binding in the assay, or to direct and control sample flow to the test region. The filtering aspect allows an analyte of interest to migrate through the device in a controlled fashion with few, if any, interfering substances. The filtering aspect, if present, often provides for a test having a higher probability of success and accuracy. In another embodiment, the sample receiving zone may also incorporate reagents useful to avoid cross-reactivity with non-target analytes that may exist in a sample and/or to condition the sample; depending on the particular embodiment, these reagents may include non-hCG blockers, anti-RBC reagents, Tris-based buffers, EDTA, among others. When the use of whole blood is contemplated, anti-RBC reagents are frequently utilized. In yet another embodiment, the sample receiving zone may incorporate other reagents such as ancillary specific binding members, fluid sample pretreatment reagents, and signal producing reagents.

In a further embodiment, the sample receiving zone is comprised of an additional sample application member (e.g., a wick). Thus, in one aspect, the sample receiving zone can comprise a sample application pad as well as a sample application member. Often the sample application member is comprised of a material that readily absorbs any of a variety of fluid samples contemplated herein, and remains robust in physical form. Frequently, the sample application member is comprised of a material such as white bonded polyester fiber. Moreover, the sample application member, if present, is positioned in fluid-flow contact with a sample application pad. This fluid flow contact can comprise an overlapping, abutting or interlaced type of contact. In occasional embodiments, the sample application member may be treated with a hydrophilic finishing. Often the sample application member, if present, may contain similar reagents and be comprised of similar materials to those utilized in exemplary sample application pads.

In another embodiment, the test device is configured to perform an immunological analysis process. In yet another embodiment, the liquid transport along the matrix is based upon capillary action. In a further embodiment, the liquid transport along the matrix is based on non-bibulous lateral flow, wherein all of the dissolved or dispersed components of the liquid sample are carried at substantially equal rates and with relatively unimpaired flow laterally through the matrix, as opposed to preferential retention of one or more components as would occur, e.g., in materials that interact, chemically, physically, ionically or otherwise with one or more components. See for example, U.S. Pat. No. 4,943,522, hereby incorporated by reference in its entirety.

One purpose of the label zone is to maintain label reagents and control reagents in a stable state and to facilitate their rapid and effective solubilization, mobilization and specific reaction with analytes of interest potentially present in a fluid sample.

In one embodiment, the label zone is comprised of a porous material such as high density polyethylene sheet material manufactured by Porex Technologies Corp. of Fairburn, Ga., USA. The sheet material has an open pore structure with a typical density, at 40% void volume, of 0.57 gm/cc and an average pore diameter of 1 to 250 micrometers, the average generally being from 3 to 100 micrometers. In another embodiment, the label zone is comprised of a porous material such as a nonwoven spunlaced acrylic fiber (similar to the sample receiving zone), e.g., New Merge or HDK material. Often, the porous material may be backed by, or laminated upon, a generally water impervious layer, e.g., Mylar. When employed, the backing is generally fastened to the matrix by an adhesive (e.g., 3M 444 double-sided adhesive tape). Typically, a water impervious backing is used for membranes of low thickness. A wide variety of polymers may be used provided that they do not bind nonspecifically to the assay components and do not interfere with flow of the fluid sample. Illustrative polymers include polyethylene, polypropylene, polystyrene and the like. On occasion, the matrix may be self-supporting. Other membranes amenable to non-bibulous flow, such as polyvinyl chloride, polyvinyl acetate, copolymers of vinyl acetate and vinyl chloride, polyamide, polycarbonate, polystyrene, and the like, can also be used. In yet another embodiment, the label zone is comprised of a material such as untreated paper, cellulose blends, nitrocellulose, polyester, an acrylonitrile copolymer, and the like. The label zone may be constructed to provide either bibulous or non-bibulous flow, frequently the flow type is similar or identical to that provided in at least a portion of the sample receiving zone. In a frequent embodiment, the label zone is comprised of a nonwoven fabric such as Rayon or glass fiber. Other label zone materials suitable for use by the present invention include those chromatographic materials disclosed in U.S. Pat. No. 5,075,078, which is herein incorporated by reference.

In a frequent embodiment, the label zone material is treated with labeled solution that includes material-blocking and label-stabilizing agents. Blocking agents include bovine serum albumin (BSA), methylated BSA, casein, nonfat dry milk. Stabilizing agents are readily available and well known in the art, and may be used, for example, to stabilize labeled reagents. In frequent embodiments, employment of the selected blocking and stabilizing agents together with labeled reagent in the labeling zone followed by the drying of the blocking and stabilizing agents (e.g., a freeze-drying or forced air heat drying process) is utilized to attain improved performance of the device.

The label zone generally contains a labeled reagent, often comprising one or more labeled reagents. In many of the presently contemplated embodiments, multiple types of labeled reagents are incorporated in the label zone such that they may permeate together with a fluid sample contacted with the device. These multiple types of labeled reagent can be analyte specific or control reagents and may have different detectable characteristics (e.g., different colors) such that one labeled reagent can be differentiated from another labeled reagent if utilized in the same device. As the labeled reagents are frequently bound to a specific analyte of interest subsequent to fluid sample flow through the label zone, differential detection of labeled reagents having different specificities (including analyte specific and control labeled reagents) may be a desirable attribute. However, frequently, the ability to differentially detect the labeled reagents having different specificities based on the label component alone is not necessary due to the presence of defined test and control zones in the device, which allow for the accumulation of labeled reagent in designated zones.

In one embodiment, a nonparticulate labeling scheme is contemplated. In these devices, a label which is a dyed antibody-enzyme complex is utilized. This dyed antibody-enzyme complex can be prepared by polymerizing an antibody-enzyme conjugate in the presence of enzyme substrate and surfactant. See, e.g., WO 9401775. Generally, the label zone contains detectible moieties comprising enzyme-antibody conjugate, particulate labeled reagents, or dye labeled reagents, metal sol labeled reagents, etc., or moieties which may or may not be visible, but which can be detected if accumulated in the test and/or control zones. The detectible moieties can be dyes or dyed polymers which are visible when present in sufficient quantity, or can be, and are preferred to be particles such as dyed or colored latex beads, liposomes, metallic or non-metallic colloids, organic, inorganic or dye solutions, dyed or colored cells or organisms, red blood cells and the like. The detectible moieties used in the assay provide the means for detection of the nature of and/or quantity of result, and accordingly, their localization in the test zones may be a function of the analyte in the sample. In general, this can be accomplished by coupling the detectible moieties to a ligand which binds specifically to an analyte of interest, or which competes with an analyte of interest for the means which permit the restraint of an analyte of interest positioned in the test zone(s). In the first approach, the detectible moieties are coupled to a specific binding partner which binds the analyte specifically. For example, if the analyte is an antigen, an antibody specific for this antigen may be used; immunologically reactive fragments of the antibody, such as F(ab')2, Fab or Fab' can also be used. These ligands coupled to the detectible moieties then bind to an analyte of interest if present in the sample as the sample passes through the labeling zone and are carried into the test region by the fluid flow through the device. When the labeled analyte reaches the capture zone, it is restrained by a restraint reagent which is analyte-specific, label/detectible moiety-specific, or ligand-specific, such as an antibody or another member of a specific binding pair. In the second approach, the conjugate or particulate moieties are coupled to a ligand which is competitive with analyte for an analyte-specific restraint reagent in a test zone. Both the analyte from the sample and the competitor bound to the detectible moieties progress with the flow of the fluid sample to the test region. Both analyte and its competitor then react with the analyte-specific restraint reagent positioned in a test zone. The unlabeled analyte thus is able to reduce the quantity of competitor-conjugated detectible moieties which are retained in the test zone. This reduction in retention of the detectible moieties becomes a measure of the analyte in the sample.

The labeling zone of immunoassay devices of the present invention may also include control-type reagents. These labeled control reagents often comprise detectible moieties that will not become restrained in the test zones and that are carried through to the test region and control zone(s) by fluid sample flow through the device. In a frequent embodiment, these detectible moieties are coupled to a member of a specific binding pair to form a control conjugate which can then be restrained in a separate control zone of the test region by a corresponding member of the specific binding pair to verify that the flow of liquid is as expected. The visible moieties used in the labeled control reagents may be the same or different color, or of the same or different type, as those used in the analyte of interest specific labeled reagents. If different colors are used, ease of observing the results may be enhanced. Generally, as used herein, the labeled control reagents are also referred to herein together with analyte specific labeled reagents or labeled test reagents as "labeled reagent(s)."

The test region is frequently comprised of a material such as cellulose, nitrocellulose, nylon, or hydrophilic polyvinylidene difluoride (PVDF). Hydrophilic polyvinylidene difluoride (PVDF) (available from Millipore, Billerica, Mass.). The term "nitrocellulose" is meant any nitric acid ester of cellulose. Thus suitable materials may include nitrocellulose in combination with carboxylic acid esters of cellulose. The pore size of nitrocellulose membranes may vary widely, but is frequently within about 5 to 20 microns, preferably about 8 to 15 microns. However, other materials are contemplated which are known to those skilled in the art. In a frequent embodiment, the test region comprises a nitrocellulose web assembly made of Millipore nitrocellulose roll laminated to a clear Mylar backing. In another embodiment, the test region is made of nylon. In less occasional embodiment, the test region is comprised of a material that can immobilize latex or other particles which carry a second reagent capable of binding specifically to an analyte, thereby defining a test zone, for example, compressed nylon powder, or fiber glass. In an occasional embodiment, the test region is comprised of a material that is opaque when in a dry state, and transparent when in a moistened state. Preferably, the test and control zones may be constructed from any of the materials as listed above for the test region. Often the test and control zones form defined components of the test region. In a particularly preferred embodiment, the test and control zones are comprised of the same material as the test region. Frequently, the term "test region" is utilized herein to refer to a region in/on a device that comprises at least the test and control zones. To provide non-bibulous flow, these materials may be and preferably are treated with blocking agents that can block the forces which account for the bibulous nature of bibulous membranes. Suitable blocking agents include bovine serum albumin, methylated bovine serum albumin, whole animal serum, casein, and non-fat dry milk, as well as a number of detergents and polymers, e.g., PEG, PVA and the like. Preferably the interfering sites on the untreated bibulous membranes are completely blocked with the blocking agent to permit non-bibulous flow there through. As indicated herein, the present disclosure envisages a test device with multiple test and control zones.

The test region generally includes a control zone that is useful to verify that the sample flow is as expected. Each of the control zones comprise a spatially distinct region that often includes an immobilized member of a specific binding pair which reacts with a labeled control reagent. In an occasional embodiment, the procedural control zone contains an authentic sample of the analyte of interest, or a fragment thereof. In this embodiment, one type of labeled reagent can be utilized, wherein fluid sample transports the labeled reagent to the test and control zones; and the labeled reagent not bound to an analyte of interest will then bind to the authentic sample of the analyte of interest positioned in the control zone. In another embodiment, the control line contains antibody that is specific for, or otherwise provides for the immobilization of, the labeled reagent. In operation, a labeled reagent is restrained in each of the one or more control zones, even when any or all the analytes of interest are absent from the test sample.

In a less occasional embodiment, a labeled control reagent is introduced into the fluid sample flow, upstream from the control zone. For example, the labeled control reagent may be added to the fluid sample before the sample is applied to the assay device. In frequent embodiments, the labeled control reagent may be diffusively bound in the sample receiving zone, but is preferably diffusively bound in the label zone.

Exemplary functions of the labeled control reagents and zones include, for example, the confirmation that the liquid flow of the sample effectively solubilized and mobilized the labeled reagents deposited in the label zone, that a sufficient amount of liquid traveled correctly through the sample receiving zone, label zone, and the test and control zones, such that a sufficient amount of analyte could react with the corresponding specific label in the label zone, migrate onto the test region comprising the test and control zones, cross the test zone(s) in an amount such that the accumulation of the labeled analyte would produce a visible or otherwise readable signal in the case of a positive test result in the test zone(s). Moreover, an additional function of the control zones may be to act as reference zones which allow the user to identify the test results which are displayed as readable zones.

Since the devices of the present invention may incorporate one or more control zones, the labeled control reagent and their corresponding control zones are preferably developed such that each control zone will become visible with a desired intensity for all control zones after fluid sample is contacted with the device, regardless of the presence or absence of one or more analytes of interest.

In one embodiment, a single labeled control reagent will be captured by each of the control zones on the test strip. Frequently, such a labeled control reagent will be deposited onto or in the label zone in an amount exceeding the capacity of the total binding capacity of the combined control zones if multiple control zones are present. Accordingly, the amount of capture reagent specific for the control label can be deposited in an amount that allows for the generation of desired signal intensity in the one or more control zones, and allows each of the control zones to restrain a desired amount of labeled control reagent. At the completion of an assay, each of the control zones preferably provide a desired and/or pre-designed signal (in intensity and form). Examples of contemplated pre-designed signals include signals of equal intensities in each control zone, or following a desired pattern of increasing, decreasing or other signal intensity in the control zones.

In another embodiment, each control zone will be specific for a unique control reagent. In this embodiment, the label zone may include multiple and different labeled control reagents, equaling the number of control zones in the assay, or a related variation. Wherein each of the labeled control reagents may become restrained in one or more pre-determined and specific control zone(s). These labeled control reagents can provide the same detectible signal (e.g., be of the same color) or provide distinguishable detectible signals (e.g., have different colored labels or other detection systems) upon accumulation in the control zone(s).

In yet another embodiment, the control zones may include a combination of the two types of control zones described in the two previous embodiments, specifically, one or more control zones are able to restrain or bind a single type of labeled control reagent, and other control zones on the same test strip will be capable of binding one or several other specific labeled control reagents.

In one embodiment, the labeled control reagent comprises a detectible moiety coupled to a member of a specific binding pair. Typically, a labeled control reagent is chosen to be different from the reagent that is recognized by the means which are capable of restraining an analyte of interest in the test zone. Further, the labeled control reagent is generally not specific for the analyte. In a frequent embodiment, the labeled control reagent is capable of binding the corresponding member of a specific binding pair or control capture partner that is immobilized on or in the control zone. Thus the labeled control reagent is directly restrained in the control zone.

In another embodiment, the detectable moiety which forms the label component of the labeled control reagent is the same detectible moiety as that which is utilized as the label component of the analyte of interest labeled test reagent. In a frequent embodiment, the label component of the labeled control reagent is different from the label component of the labeled test reagent, so that results of the assay are easily determined. In another frequent embodiment, the control label and the test label include colored beads, e.g., colored latex. Also frequently, the control and test latex beads comprise different colors.

In a further embodiment, the labeled control reagent includes streptavidin, avidin or biotin and the control capture partner includes the corresponding member of such specific binding pairs, which readily and specifically bind with one another. In one example, the labeled control reagent includes biotin, and the control capture partner includes streptavidin. The artisan will appreciate that other members of specific binding pairs can alternatively be used, including, for example, antigen/antibody reactions unrelated to analyte.

The use of a control zone is helpful in that appearance of a signal in the control zone indicates the time at which the test result can be read, even for a negative result. Thus, when the expected signal appears in the control line, the presence or absence of a signal in a test zone can be noted.

In still further embodiment, a control zone comprising a mark that becomes visible in the test region when the test regions is in a moist state is utilized. Control zones of this type are described in U.S. patent application Ser. No. 09/950,366, filed, Sep. 10, 2001, currently pending and published as U.S. Patent Application Publication No. 20030049167, and Ser. No. 10/241,822, filed Sep. 10, 2002, currently pending and published as U.S. Patent Application Publication No. 20030157699.

In occasional embodiments, one or more control zones of this type are utilized. In another embodiment, a combination of control zones of the type utilizing labeled control reagents and control zone and of the type that display the control zone when in a moist state can be used. This allows a simple way to formulate control zones while allowing to use a reagent-based control zone to ascertain that the re-solubilization and mobilization of the reagents in the label pad process has been effective, and that the specific reactions took place as expected, all along the path defined by the sample pad, label pad, test strip and absorbent pad. The present embodiment includes the use of one or more control zones that become visible when the test region is in the moist state for each of the control zones of an assay, except the control zone on the distal or downstream end of the test strip.

As indicated above, labeled test reagents are further provided which frequently comprise a test label coupled to a member of a specific binding pair that is capable of specifically binding an analyte of interest. Thus, in general, multiple labeled test reagents are positioned in the label zone, each of which is specific for a predetermined analyte of interest.

Test zones of the present description include means that permit the restraint of an analyte of interest. Frequently, test zones of the present description include a ligand that is capable of specifically binding to an analyte of interest. Alternatively, test zones of the present description include a ligand that is capable of specifically binding the labeled reagent bound to an analyte of interest. In practice, a labeled test reagent binds an analyte of interest present in a fluid sample after contact of the sample with a representative device and flow of the fluid sample into and through the label zone. Thereafter, the fluid sample containing the labeled analyte progresses to a test zone and becomes restrained in the test zone. The accumulation of labeled analyte in the test zone produces a detectible signal. Frequently, devices of the present disclosure incorporate one or more test zones, each of which is capable of restraining different analytes, if present, in a fluid sample. Thus, in representative embodiments two, three, four, five or more (labeled) analytes of interest can be restrained in a single or different test zones, and thereby detected, in a single device.

The present devices may optionally further comprise an absorbent zone that acts to absorb excess sample after the sample migrates through the test region. The absorbent zone, when present lies in fluid flow contact with the test region. This fluid flow contact can comprise an overlapping, abutting or interlaced type of contact. In an occasional embodiment, a control region (end of assay indicator) is provided in the absorbent zone to indicate when the assay is complete. In this embodiment, specialized reagents are utilized, such as pH sensitive reagents (such as bromocresol green), to indicate when the fluid sample has permeated past all of the test and control zones. Alternatively, the end of assay control region may be effected by applying a line of soluble ink on the test region after all of the test and control zones, and at the interface with the absorbent zone. In general, the liquid front moving through the capture zone will solubilize the ink and transfer it into the absorbent. The resulting color change will be seen in an observation window above the absorbent zone, signifying end of assay. Thus, these types of control regions are not specific for a particular analyte. Generally, the absorbent zone will consist of an absorbent material such as filter paper, a glass fiber filter, or the like.

In an occasional embodiment, the fluid sample must be processed or treated prior to contact with the device to ensure accurate detection of at least one of the multiple analytes of interest. In this embodiment, a reagent, such as an extraction solution, may be used to prepare the sample. Alternatively, reagents can be added to the test device after initial contact with the fluid sample. For example, the sample is introduced to the device, and thereafter a reagent, such as a developer solution, is added to complete the assay.

FIG. 1 provides various representative configurations of the presently contemplated devices. Although not specifically limited to dipstick type assays, these configurations may be incorporated in a dipstick-type assay among other types of immunoassay devices contemplated herein. The arrow in each Figure indicates the general direction of fluid sample flow after initial contact with the device. The boxes containing vertical lines and/or the diagonal lines depict control zones, and the boxes containing crosshatched lines depict test zones. The sample receiving zone [1], the label zone [2] and the test region [3] are also depicted. The present disclosure is not intended to be limited to the configurations depicted in FIG. 1(A-J). These views are merely provided for illustrative purposes. For example, the test and control zones are not necessarily of the same shapes and sizes depicted in FIG. 1. Further, the sample receiving zone, the label zone and test region are not necessarily presented to scale. FIG. 1A depicts a device having two test zones and a single control zone, wherein the control zone is situated between the test zones within the flow path. FIG. 1B depicts a device having three test zones and two control zones, wherein the control zones are situated between the test zones within the flow path. Further, in FIG. 1B, the second test zone is situated between the two control zones within the flow path. FIG. 1C depicts a device having four test zones and two control zones, wherein the control zones are situated between the test zones within the flow path. Further, in FIG. 1C, the second and third test zones are adjacent without a control zones between these zones. FIG. 1D depicts a device having two test zones and a single control zone, wherein the control zone is situated downstream of the test zones within the flow path. FIG. 1E depicts a device having two test zones and a single control zone, wherein the control zone is situated upstream of the test zones within the flow path. FIG. 1F depicts a device having four test zones and three control zones, wherein the control zones are situated between the test zones within the flow path in a alternating fashion. FIG. 1G depicts a device having five test zones and one control zone, wherein the control zone is situated between the second to last and last test zones within the flow path. Further, in FIG. 1G, the first through fourth test zones are adjacent to one another without having control zones between each test zone. FIG. 1H depicts a device having three test zones and one control zone, wherein the control zone is situated between the second and third test zones within the flow path. FIG. 1I depicts a device having four test zones and three control zones (wherein two control zones are comprised of the same labeled-control reagent and binding reagent specific pair (or alternatively, are comprised of motifs that become visible when the test zone is moist), but one control zone (as indicated by the diagonal lines) is comprised of one distinct pair of labeled control reagent and control zone binding reagent). FIG. 1J depicts a device having four test zones and three control zones (wherein one control zone is comprised of the same labeled-control reagent and binding reagent specific pair (or alternatively, are comprised of motifs that become visible when the test zone is moist), but two control zones (as indicated by the diagonal lines) are comprised of one distinct pair of labeled control reagent and control zone binding reagent). Frequently, when two types of control zones or pairs of control zones reagents are used, each control zone may be colored differently. Other device configurations within the scope of the present disclosure are contemplated. For example, although not depicted, the present disclosure contemplates a device having one test zone and one control zone, wherein multiple analytes can be detected within the test zone.

Those of skill in the art will recognize that a variety of direct and indirect assay formats may be employed in the present devices. In a frequent embodiment, a direct assay format is utilized. Direct assays are exemplified by those that detect the presence of an antigen in a sample, as well as those that detect the presence of an antibody in a sample.

As provided above, particular devices of the present invention include a support. The support in these devices provides a convenient platform for performance of the assay. However, the composition and shape of the support are not critical and may vary. Occasionally, the support may be comprised of a plastic or nylon material.

In frequent embodiment, the present devices are in the form of a dipstick. Generally, dipsticks of the present invention are functionally analogous to the lateral assays described herein excepting the method of contacting a fluid sample. In embodiments configured as a dipstick, the matrix and support will generally be located on one end of the dipstick. The configuration of such devices will allow the device to be dipped or contacted with a fluid sample with one end of a matrix i.e., the sample receiving zone. After contacting the fluid sample, the sample preferably migrates in an axial flow path through the matrix from the sample receiving zone to the label zones and test region. Alternatively, the devices of the present invention may be shaped so that samples may be applied to the device by means other than dipping, e.g., application of controlled amounts of sample by pipettes or the like.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

EXAMPLES

Exemplary Test Device for Distinguishing Influenza A from Influenza B

An immunoassay device for use in determining the presence of and distinguishing between multiple analytes was constructed in accordance with the present invention. In particular, an immunoassay dipstick capable of diagnosing influenza and distinguishing between influenza A and influenza B infection was prepared. Those of skill in the art are familiar with the general methods for preparation of immunoassay dipstick devices (see, e.g., U.S. Pat. No. 5,712,172) as well as other lateral flow immunoassays. The exemplary device described herein may likewise be so constructed.

The exemplary test device comprised a sample pad containing sample conditioning reagents, a label pad containing monoclonal antibody against Influenza A nucleoprotein covalently bound to red colored latex microparticles (Duke Scientific), a monoclonal antibody against Influenza B nucleoprotein covalently bound onto red colored latex microparticles, and an unrelated protein (in this example, biotinylated BSA) bound to blue latex microparticles (Duke Scientific). The device was assembled, in order, as a sample pad in fluid communication with a label pad in fluid communication with a test pad (observation zone) in fluid communication with an absorbent pad at the device end. The pads were laminated, using 3M adhesive, onto a Mylar backing, in sequence and in fluid communication to allow lateral flow from one pad to the next. A strip of plastic material, comprising a cutout ("window") over the observation zone, was then laminated on top of the device leaving a portion of the sample pad exposed for sample application.

This plastic cover served the purpose of securing the pads in place and in overlapping contact with one another, so that fluid communication was maintained there between. Additionally, the plastic material was selected to provide sufficient rigidity to the final device to allow convenient handling by the user and to isolate the areas of the dipstick that are moistened during the testing process.

The observation zone was made of a Highflow Plus nitrocellulose membrane from Millipore laminated onto a white Mylar backing. Test and control reagents were deposited, using standard techniques, onto the observation zone membrane in the form of 3 lines, each perpendicular to the flow of sample and in order upstream to downstream as follows: anti-Flu B monoclonal antibodies against a second epitope of the Influenza B nucleoprotein at a concentration of about 3 mg/ml in phosphate buffer was deposited as the a first test zone; at about 3 mm downstream of the first test zone, a control zone was formed by depositing streptavidin labeled BSA; and at about 3 mm downstream of the first control zone a second test zone was formed by depositing an antibody against a second epitope of the Influenza A nucleoprotein (again, at a concentration of about 3 mg/ml in phosphate buffer). Thus, the two test zones and one control zone were configured as illustrated in FIG. 1A.

Once the test and control reagents were deposited and dried onto the nitrocellulose membrane, the membrane was rendered non-bibulous by treatment with a blocking solution. As discussed above, non-bibulous flow allows the components of interest in the assay to move at substantially the same rate along the test strip without preferential retention of such components. This facilitates flow of a sufficient quantity of labeled material across the test and control zones, such that positioning of the control line upstream of the second test line does not interfere with the effectiveness or reliability of the control zone.

At the end of the test device, the observation zone is in fluid contact with a pad of absorbent material, in this example, made of absorbent cellulosic paper (Whatman).

As is common in the industry, the concentration of each component was optimized during development of the test to allow the assay to reach the required sensitivity while avoiding non-specific binding. For instance, the colored latex/anti-Influenza A antibody conjugate was diluted serially and deposited onto label pads that were dried, assembled into functional strips, and tested with liquid samples of the viral nucleoprotein at concentrations ranging from 7.5 ng/ml to 100 ng/ml. The lowest concentration of conjugate allowing detection of the 7.5 ng/ml solution of the nucleoprotein was selected as optimal. The optimal concentration of anti-Influenza B antibody/colored latex conjugate was similarly optimized. The optimum concentration of the control protein/colored latex conjugate was selected to provide a line clearly visible to the eye after normal incubation of the assay. To construct the final product, the optimized label (conjugate) solutions were mixed together then applied to and dried on the label pad using standard techniques.

The size/capacity of the absorbent pad was optimized to ensure that a sufficient amount of sample liquid would move through the test strip and across the two test and one control zones to product a visible, accurate signal when as little as 7.5 ng/ml of Influenza A and 7.5 ng/ml of Influenza B nucleoproteins were present in the sample.

Test of Exemplary Device

To confirm that positioning of a control zone upstream of a test zone would not compromise the accuracy of a device according to the present invention, two devices were created and compared to one another. Both devices were constructed as described above, except that each was constructed with only an Influenza A test zone (single analyte). In one device, the control zone was located upstream of the test zone and in the second device the control zone was located downstream of the test zone. A sample of Influenza A nucleoprotein at a relatively low concentration (sufficient to generate a visible signal of about 0.030 O.D. measured on an optical density scanner after a 10 minute incubation) was prepared and applied to each device. FIG. 2 shows the ratios between the O.D. values of the test zone and the control zone for different volumes of sample for each of the two devices. Increasing sample volumes were used, ranging from 25 uL up to 300 uL, facilitating identification of the minimum sample volume required to generate sufficient signal for the assay to meet design specifications. The graph in FIG. 2 clearly shows that the ratios of the signals generated by the test zone and control zone in the two devices are virtually identical regardless of the position of the test zone relative to the control zone.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims. Citation herein of publications or documents is not intended as an admission that any of the foregoing is pertinent prior art.

What is claimed is:

1. A method for the detection of multiple nucleic acid analytes in a fluid sample, the method comprising:
   contacting a device with a fluid sample suspected of comprising one or more nucleic acid analytes of interest, each nucleic acid analyte of interest bound to a haptenic complementary nucleotide sequence, the device comprising a matrix defining an axial flow path, the matrix comprising:
   i) a sample receiving zone at an upstream end of the axial flow path that receives the fluid sample,
   ii) a label zone positioned within the axial flow path and downstream from the sample receiving zone, said label zone comprising a mobilizable signal producing component that binds each nucleic acid analyte of interest bound to its haptenic complementary nucleotide sequence,
   iii) at least two test zones positioned within the axial flow path and downstream from the label zone, wherein each test zone comprises a restraining component that restrains each nucleic acid analyte of interest bound to its haptenic complementary nucleotide sequence, and
   iv) a control zone positioned within the axial flow path and downstream from the label zone, the control zone comprising an immobilized member of a specific binding pair that binds with a control reagent deposited on the matrix; and
   inspecting the at least two test zones for signal producing component captured by the restraining component at each of the at least two test zones, where presence of the signal producing component at a test zone indicates presence of the nucleic acid analyte of interest bound to its haptenic complementary nucleotide sequence.

2. The method of claim 1, wherein the mobilizable signal producing component is selected from the group consisting of a chemiluminescent agent, a particulate label, a colorimetric agent, an energy transfer agent, an enzyme, a fluorescent agent and a radioisotope.

3. The method of claim 1, wherein the mobilizable signal producing component is a colored particulate label.

4. The method of claim 1, wherein the label zone comprises a mobilizable signal producing component comprised of different colored particulate labeled reagents.

5. The method of claim 1, wherein the mobilizable signal producing component is a fluorescent agent.

6. The method of claim 1, wherein the restraining component in one test zone of said at least two test zones is an antibody that binds a nucleic acid analyte of interest bound to a haptenic complementary nucleotide sequence.

7. The method of claim 1, wherein the immobilized member in the control zone comprises an antibody.

8. The method of claim 7, wherein the antibody in the control zone is specific for a labeled control reagent.

9. The method of claim 1, wherein the nucleic acid analyte of interest is associated with a sexually transmitted disease.

10. The method of claim 9, wherein the nucleic acid analytes of interest are for detection of herpes.

11. The method of claim 1, wherein the device is in the form of a dipstick assay device.

12. The method of claim 1, where inspecting the at least two test zones for signal producing component comprises inspecting via direct visual, non-instrument for presence of a signal detectable.

13. The method of claim 1, wherein said label zone comprising a mobilizable signal producing component that binds the haptenic complementary nucleotide sequence.

14. A method for the detection of multiple analytes in a fluid sample, the method comprising:
    contacting a device with a fluid sample suspected of containing one or more analytes of interest, the device comprising a matrix comprising:
    i) a sample receiving zone that receives the fluid sample,
    ii) a label zone downstream from the sample receiving zone, said label zone comprising a mobilizable signal producing component that binds an analyte of interest,
    iii) at least two test zones, wherein each of the at least two test zones comprises a component for restraint of a different labeled analyte of interest, and
    iv) two or more control zones, wherein at least one of the control zones is positioned downstream of a test zone in the at least two test zones, and wherein at least one of the control zones is a reference zone to provide an indication of the relative location of one or more of the at least two test zones; and
    detecting one or more labeled analytes of interest restrained in the one or more test zones.

15. The method of claim 14, wherein the device comprises three or more test zones.

16. The method of claim 14, wherein each of the test zones contains an immobilized reagent capable of specifically binding a unique analyte.

17. The method of claim 14, wherein each of the test zones contains an immobilized reagent capable of specifically binding a unique labeled reagent.

18. The method of claim 14, wherein the mobilizable signal producing component in the label zone is a fluorescent agent.

19. A method for the detection of multiple analytes in a fluid sample, the method comprising:
    contacting a device with a fluid sample suspected of containing one or more analytes of interest, the device comprising a matrix comprising:
    i) a sample receiving zone that receives the fluid sample,
    ii) a label zone downstream from the sample receiving zone, said label zone comprising a first labeled reagent and a second labeled reagent, each of said labeled reagents capable of binding an analyte to form a labeled analyte and mobilizable in the presence of fluid sample,
    iii) at least two test zones downstream from the label zone, wherein each of the at least two test zones comprises a component for restraint of a different labeled analyte of interest, and
    iv) two or more control zones, wherein at least one of the control zones is positioned downstream of a test zone in the at least two test zones, and wherein at least one of the control zones is a reference zone to provide an indication of the relative location of one or more of the at least two test zones; and
    inspecting the at least two test zones for labeled analyte.

20. The method of claim 19, wherein at least one of the control zones contains a component for restraint that provides for the immobilization of the first labeled reagent or the second labeled reagent.

21. The method of claim 19, wherein each of the test zones comprises an immobilized reagent capable of specifically binding a unique analyte in the one or more analytes of interest.

22. The method of claim 21, wherein the first labeled reagent and the second labeled reagent are fluorescent agents.

* * * * *